United States Patent
Janke et al.

(10) Patent No.: US 6,774,163 B2
(45) Date of Patent: Aug. 10, 2004

(54) FLAME RETARDANTS FOR POLYMERS COMPRISING A MIXTURE OF TWO DIFFERENT ARYL PHOSPHATES, THEIR PREPARATION AND THEIR USE

(75) Inventors: Nikolaus Janke, Dormagen (DE); Otto Mauerer, Leichlingen (DE); Manfred Pieroth, Köln (DE)

(73) Assignee: Bayer Chemicals AG, Leverkusen (DE)

( * ) Notice: Subject to any disclaimer, the term of this patent is extended or adjusted under 35 U.S.C. 154(b) by 0 days.

(21) Appl. No.: 10/412,505

(22) Filed: Apr. 11, 2003

(65) Prior Publication Data

US 2003/0195281 A1 Oct. 16, 2003

(30) Foreign Application Priority Data

Apr. 16, 2002 (DE) .......................................... 10216736

(51) Int. Cl.$^7$ ............................................. C08K 5/523
(52) U.S. Cl. ........................ 524/127; 524/137; 524/140; 524/141; 524/145; 252/609
(58) Field of Search ................................. 524/127, 137, 524/140–141, 145; 252/609

(56) References Cited

U.S. PATENT DOCUMENTS

| | | | |
|---|---|---|---|
| 3,192,242 A | 6/1965 | Birum et al. ................ | 524/118 |
| 3,689,602 A | 9/1972 | Ismail ......................... | 524/108 |
| 5,278,212 A | 1/1994 | Nishihara et al. ............ | 524/141 |
| 5,728,859 A | 3/1998 | Bright et al. ................. | 558/99 |
| 5,932,637 A * | 8/1999 | Ito et al. ...................... | 523/451 |
| 5,952,408 A * | 9/1999 | Lee et al. ..................... | 524/127 |
| 6,025,421 A * | 2/2000 | Atarashi et al. ............. | 524/151 |
| RE36,902 E | 10/2000 | Eckel et al. ................. | 524/127 |
| 6,319,432 B1 * | 11/2001 | Harrod et al. ............... | 252/609 |
| 6,403,819 B1 | 6/2002 | Bright et al. ................. | 558/99 |
| 2002/0147256 A1 | 10/2002 | Eckel et al. ................. | 524/115 |

FOREIGN PATENT DOCUMENTS

| | | | |
|---|---|---|---|
| CA | 2139726 | * | 7/1995 |
| DE | 24 56 532 | | 6/1975 |
| DE | 44 00 441 | | 7/1995 |
| EP | 509506 A | | 10/1992 |
| EP | 662495 A | | 7/1995 |
| GB | 1 487 609 | | 10/1977 |

* cited by examiner

Primary Examiner—Peter Szekely
(74) Attorney, Agent, or Firm—Godfried R. Akorli; Diderico VanEyl

(57) ABSTRACT

The present invention relates to a novel flame retardant system for polymers comprising a mixture of two different aryl phosphates, to its preparation, and to its use.

23 Claims, No Drawings

FLAME RETARDANTS FOR POLYMERS COMPRISING A MIXTURE OF TWO DIFFERENT ARYL PHOSPHATES, THEIR PREPARATION AND THEIR USE

BACKGROUND OF THE INVENTION

1. Field of the Invention

The present invention relates to a novel flame retardant system for polymers comprising a mixture of two different aryl phosphates, to its preparation, and to its use.

2. Brief Description of the Prior Art

The high combustibility of many polymers means that they have to be provided with flame retardants. One way of increasing the flame retardancy of polymers is to add incombustible or low-combustibility fillers, such as glass, powdered quartz, wollastonite, etc. Another way is to use inorganic flame retardants. Examples which may be mentioned are boron compounds and metal hydroxides. However, large amounts of these types of flame retardants have to be used for adequate flame retardancy. This leads to major problems in the production and processing of polymers.

Use of halogenated compounds is very widespread, examples being tetrabromo-bisphenol A or the corresponding bisepoxide derived therefrom, decabromodiphenyl ether, and brominated polystyrenes. However, the use of halogenated flame retardants is controversial. During combustion corrosive gases such as hydrogen chloride or hydrogen bromide can be produced. There is also a risk that severely toxic dioxin-like products are formed.

U.S. Pat. Nos. 3,689,602, 3,192,242, GB-A-1 487 609 and EP-A-465 605 disclose the use of halogen-containing and also halogen-free phosphates as flame retardants for polymers. However, organophosphorus compounds which are not incorporated into the polymer matrix have plasticizing properties. Large amounts of these phosphorus compounds have to be added in order to achieve effective flame retardancy, and they therefore impair the mechanical and electrical properties of the polymers to an unacceptable degree for many applications.

For example, the strength values and/or the glass transition point are lowered. In addition, some of these compounds are thermally unstable or unstable with respect to hydrolysis. The halogen-containing phosphates are moreover controversial from an environmental point of view, as mentioned above.

It is known that the use of certain aryl thiophosphates or aryl phosphates containing certain functional groups brings about an increase in the flame retardancy of polymers, in particular resins, such as epoxy resins, without substantially impairing their thermal and mechanical properties.

DE-A-44 00 441 has previously disclosed the sole use of the aryl phosphates (termed "aryl phosphate type I" hereinafter) containing functional groups. However, there was a need to make further improvement in the use of aryl phosphates as flame retardants for polymers according to DE-A-44 00 441. For example, these aryl phosphates have never been able to pass a fire test to the UL 94 standard. Furthermore, glass transition temperatures above 150° C. were generally achieved using a combination of aryl phosphates type I and a further amine hardener. Resins which comprise solely this aryl phosphate generally begin to soften at from 130 to 140° C. These temperatures are too low for use in electrical devices or in printed circuits ("printed circuit boards"). Another disadvantage of DE-A-44 00 441 is that the aryl phosphates described therein discolour the polymers.

An object on which the invention was based was to provide a flame retardant which can be used for polymers and which has at least one of the following properties: high glass transition temperatures and/or markedly less discoloration/yellowing and/or, required for flame retardancy, a very high phosphorus content, the flame retardant being used in polymers and in particular in epoxy resins.

SUMMARY OF THE INVENTION

The invention provides a mixture comprising aryl phosphates type I of the general formula (I)

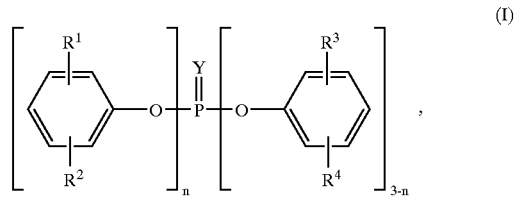

where $R^1$ to $R^4$, independently of one another, are hydrogen, alkyl, cycloalkyl, alkenyl, aralkyl or aryl, where the aryl moiety may be unsubstituted or have alkyl substitution, Y is oxygen or sulphur, X is OH, SH, COOH, COOR$^5$, NH$_2$, NHR$^6$, NR$^6$R$^7$ or CN, where $R^5$ to $R^7$, independently of one another, are as defined for $R^1$ to $R^4$, and n is 0, 1 or 2, and aryl phosphates type II of the general formula (II)

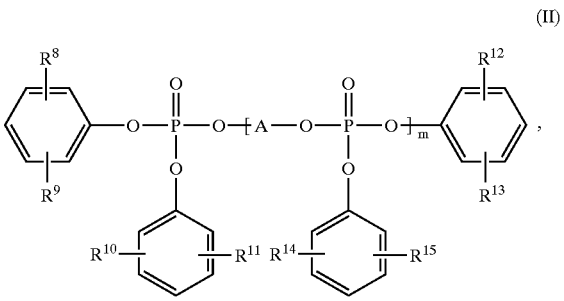

where $R^8$ to $R^{15}$, independently of one another, are hydrogen, alkyl, cycloalkyl, alkenyl, aralkyl or aryl, where the aryl moiety may be unsubstituted or have alkyl substitution, m is 0, 1, 2 or 3 and A is aromatics which contain at least two functional groups.

DETAILED DESCRIPTION OF THE INVENTION

Particular alkyl radicals $R^1$ to $R^4$ which may be used for the aryl phosphates type I are those having from 1 to 20 carbon atoms, preferably from 1 to 6 carbon atoms, particularly preferably from 1 to 4 carbon atoms. The cycloalkyl radicals preferably have from 5 to 8 ring carbon atoms, in particular 5 or 6 ring carbon atoms, and the alkenyl radical may be linear or branched and contain from 2 to 12 carbon atoms, preferably from 2 to 6 carbon atoms. Preferred aralkyl groups are those containing from 7 to 12 carbon atoms. Preferred aryl radicals used are those with substitution by $C_1$–$C_4$-alkyl radicals and having from 6 to 14 ring carbon atoms. The aryl radicals may also be unsubstituted.

Examples of the radicals $R^1$ to $R^4$ of the aryl phosphates type I are: methyl, ethyl, propyl, isopropyl, n-butyl, isobutyl, tert-butyl, pentyl, hexyl, octyl, dodecyl, tetradecyl, eicosyl, cyclopentyl, cyclohexyl, methylcyclohexyl, vinyl, prop-1-enyl, prop-2-enyl, n-but-3-enyl, n-pent-4-enyl, n-hex-5-enyl, phenyl, naphthyl, biphenyl, benzyl, methylbenzyl, phenylethyl.

The use of these aryl phosphates of type I is particularly preferred when X is $NH_2$, the radicals $R^1$ to $R^4$ are hydrogen and n is 0, 1 or 2.

Particular alkyl radicals $R^8$ to $R^{15}$ which may be used for the aryl phosphates type II are those having from 1 to 20 carbon atoms, preferably from 1 to 6 carbon atoms, particularly preferably from 1 to 4 carbon atoms. The cycloalkyl radicals preferably have from 5 to 8 ring carbon atoms, in particular 5 or 6 ring carbon atoms, and the alkenyl radical may be linear or branched and contain from 2 to 12 carbon atoms, preferably from 2 to 6 carbon atoms. Preferred aralkyl groups are those containing from 7 to 12 carbon atoms. Preferred aryl radicals used are those with substitution by $C_1$–$C_4$-alkyl radicals and having from 6 to 14 ring carbon atoms. The aryl radicals may also be unsubstituted.

Examples of the radicals $R^8$ to $R^{15}$ of the above formula are: methyl, ethyl, propyl, isopropyl, n-butyl, isobutyl, tert-butyl, pentyl, hexyl, octyl, dodecyl, tetradecyl, eicosyl, cyclopentyl, cyclohexyl, methylcyclohexyl, vinyl, prop-1-enyl, prop-2-enyl, n-but-3-enyl, n-pent-4-enyl, n-hex-5-enyl, phenyl, naphthyl, biphenyl, benzyl, methylbenzyl, phenylethyl.

The aryl phosphates type II may be unbridged, and here m is preferably 0. The aryl phosphates type II are preferably bridged, m being 1, 2 or 3. Examples of unbridged aryl phosphates type II are triphenyl phosphate and alkylphenyl phosphates.

As A, preference is given to a radical which in the form of $A(OH)_2$ is the compound bisphenol A or resorcinol.

Very particular preference is given to aryl phosphates type II in which $R^8$ to $R^{15}$ are methyl and A is a radical which in the form of $A(OH)_2$ is bisphenol A.

Some of the compounds are known or may be prepared by known methods. One way of preparing the aryl phosphates type I is transesterification of an appropriate triaryl phosphate with the appropriate phenols in a suitable molar ratio with basic catalysis (Houben-Weyl, Methoden der organischen Chemie [Methods of organic chemistry], Volume 12/2, pp. 371 et seq., Georg Thieme Verlag, Stuttgart, 1964).

Some of the aryl phosphates type II, e.g. diphenyl cresyl phosphate or bisphenol A bis(diphenyl) phosphate, are commercially available products with the trade names Disflamoll DPK® and Fyrolflex BDP®, respectively, from Bayer or Akzo. Bridged phosphates, e.g. dixylenyl bisphenol A diphosphate (hereinafter "bisphenol A bis (dixylenylphosphate)"), may be prepared by bridging of $POCl_3$ with multi-functional aromatics and reaction of suitable phenols. Examples of a preparation are described in EP-A-509 506 and EP-A-764 650.

The mixture preferably comprises amounts of from 3 to 98% by weight, preferably from 13 to 93% by weight, particularly preferably from 25 to 88% by weight, of aryl phosphates type I and amounts of from 2 to 97% by weight, preferably from 7 to 87% by weight, particularly preferably from 12 to 75% by weight, of the aryl phosphates type II, based in each case on the entirety of aryl phosphate type I and aryl phosphate type II. The mixture preferably comprises from 70 to 100% by weight, particularly preferably from 90 to 100% by weight, very particularly preferably from 95 to 100% by weight, of aryl phosphates type I and aryl phosphates type II, based on the mixture.

The invention further provides a process for preparing the inventive aryl phosphate mixture, characterized in that aryl phosphates type I of the general formula (I)

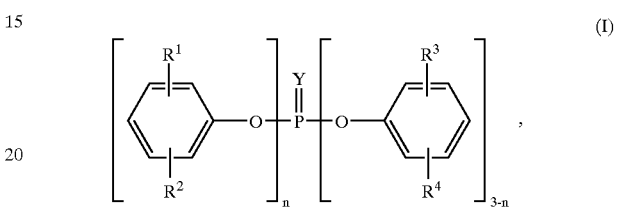

where $R^1$ to $R^4$, Y, X and n are as defined above, and aryl phosphates type II of the general formula (II)

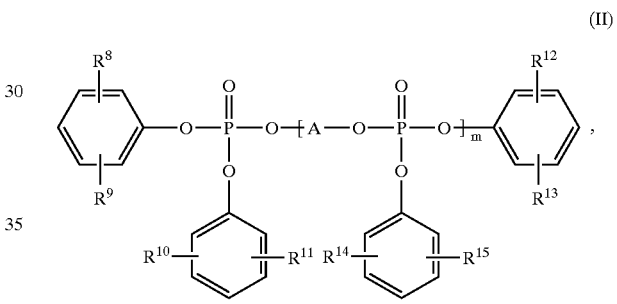

where $R^8$ to $R^{15}$, A and m are as defined above, are mixed.

The invention further provides a process for preparing polymers provided with flame retardants, characterized in that either the aryl phosphate mixture or the aryl phosphates type I and II is/are separately incorporated into the polymer.

The ideal amounts of the inventive aryl phosphate mixture for the polymer depend on the nature of the polymers and the nature of the aryl phosphates used of type I and II, and may easily be determined by appropriate preliminary experiments. Even very small added amounts of the inventive aryl phosphate mixture are generally effective, meaning that the mixture has practically no effect on the thermal and mechanical properties of the polymers to be rendered flame-retardant.

The inventive aryl phosphate mixture may be used in various physical forms, depending on the type of polymer used and on the desired properties. For example, it may be ground to give a fine-particle form in order to achieve better dispersion in the polymer. Mixtures of the inventive aryl phosphate mixture may also be used. The aryl phosphates of the formula I and aryl phosphates of the formula II may moreover be dissolved in a suitable solvent, e.g. butanone, and this solution may then be added to the polymer.

The amounts of the aryl phosphate mixture usually incorporated into the polymer are from 2 to 80% by weight, preferably from 6 to 60% by weight, particularly preferably from 10 to 50% by weight, based on the polymer. In the case of separate addition, the amounts of aryl phosphate type I incorporated into the polymer are usually from 1 to 50% by weight, preferably from 3 to 40% by weight, particularly preferably from 5 to 35% by weight, and the amounts of the aryl phosphate type II incorporated into the polymer are preferably from 1 to 30% by weight, with preference from 3 to 20% by weight, particularly preferably from 5 to 15% by weight, based on the polymer.

The temperature at which the aryl phosphate mixture or the aryl phosphates type I and II is/are separately incorporated into the polymers is generally from 20 to 200° C., preferably from 20 to 80° C.

Examples of polymers which may be rendered flame-retardant using the inventive aryl phosphate mixture are:

1. Polyphenylene oxides and polyphenylene sulphides, and also mixtures of these polymers with polystyrene graft polymers or with styrene copolymers such as high-impact polystyrene or with EPDM copolymers or with rubbers, and also mixtures of polyphenylene oxides with polyamides and polyesters.
2. Polyurethanes derived from polyethers, from polyesters or from polybutadiene with terminal hydroxy groups on the one hand and from aliphatic or aromatic polyisocyanates on the other hand, including polyisocyanurates and precursors of these.
3. Polyamides and copolyamides derived from diamines and dicarboxylic acids and/or from aminocarboxylic acids or from the corresponding lactams, for example nylon-4, nylon-6, nylon-6/6, nylon-6/10, nylon-11, nylon-12, poly-2,4,4-trimethylhexamethyleneterephthalamide or poly-m-phenyleneiso-phthalamide, and also copolymers of these with polyethers, e.g. with polyethylene glycols, with polypropylene glycols or with polytetramethylene glycols.
4. Polyesters derived from dicarboxylic acids and dialcohols and/or hydroxy-carboxylic acids or the corresponding lactones, e.g. polyethylene tere-phthalate, polybutylene terephthalate, poly-1,4-dimethylolcyclohexane tere-phthalate and polyhydroxybenzoates, and also block copolyether esters derived from polyethers with terminal hydroxy groups.
5. Unsaturated polyesters derived from copolyesters of saturated and unsaturated dicarboxylic acids and polyhydric alcohols and vinyl compounds as cross-linkers.
6. Polystyrene.
7. Graft copolymers of styrene, e.g. styrene on polybutadiene, styrene and acrylonitrile on polybutadiene, styrene and alkyl(meth)acrylates on poly-butadiene, styrene and acrylonitrile on ethylene-propylene-diene terpolymers, styrene and acrylonitrile on acrylate-butadiene copolymers, and also mixtures of these with random copolymers of styrene or α-methylstyrene with dienes or with acrylic acid derivatives, e.g. the styrene terpolymers known as ABS, MBS, or ASA.
8. Polycarbonates.
9. Epoxy resins derived from polyepoxides, e.g. from diepoxides, in particular from bisphenol A diepoxides, or from cycloaliphatic diepoxides.
10. Phenolic resins and melamine resins and blends of these.

The polymers provided with the inventive aryl phosphate mixtures may also comprise other conventional additives, e.g. heat stabilizers, light stabilizers, UV absorbers, antioxidants, antistats, preservatives, coupling agents, fillers, pigments, lubricants, foaming agents, fungicides, plasticizers, processing aids, other flame-retardant additives and agents to reduce smoke generation. Examples of other flame-retardant additives which may be used are phosphorus-containing salts, e.g. ammonium polyphosphates, melamine and melamine salts, antimony trioxide, aluminium hydroxide, bismuth phosphate, molybdenum oxide, and mixtures of these compounds with zinc oxide and/or with magnesium oxide, or with zinc salts and/or with magnesium oxide salts.

In one preferred embodiment of the process for preparing polymers provided with flame retardant, the polymer is an epoxy resin. Particular preference is given to epoxy resins such as bisphenol A epoxy resins, bisphenol F epoxy resins, phenol novolac epoxy resins, and cresol novolac epoxy resins (see, for example, Houben-Weyl, Methoden der organischen Chemie [Methods of organic chemistry], Vol. E 20/3, pp 1891 et seq., Georg Thieme Verlag, Stuttgart N.Y., 1987).

Advantages of the inventive aryl phosphate mixture for providing flame retardancy to, for example, epoxy resins are that it is possible to achieve the high phosphorus content required for flame retardancy in the moulding composition, yellowing of the moulding composition after curing is lessened, and that they can be used, alone or together with conventional hardeners, for epoxy resins.

Although use may be made of any of the known hardeners for epoxy resins, preference is given to anhydride hardeners and amine hardeners, as described, for example, in Houben-Weyl, Methoden der organischen Chemie [Methods of organic chemistry], Vol. E 20/3, pp 1950 et seq., Georg Thieme Verlag, Stuttgart N.Y., 1987. Examples of anhydride hardeners are: phthalic anhydride, hexahydrophthalic anhydride, methyltetrahydrophthalic anhydride, ethylhexahydrophthalic anhydride and methylnadic anhydride. Suitable amine hardeners are dicyandiamide, 4,4'-diaminodiphenylmethane, 4,4'-diaminodiphenyl sulphone, or $BF_3$ monoethylamine complex. If the inventive aryl phosphate mixtures are used together with the abovementioned conventional hardeners, it is then preferable that the hardener mixtures to be added to the epoxy resins comprise from 10 to 100% by weight, particularly preferably from 50 to 100% by weight, of the inventive aryl phosphate mixture and from 0 to 90% by weight, particularly preferably from 0 to 50% by weight, of one of the anhydride hardeners and/or amine hardeners mentioned, where the total of the % by weight of the aryl phosphate mixture and the anhydride and/or amine hardener has to be 100% by weight.

Polymers provided with flame retardants are usually prepared by reacting liquid or soluble polymers, in particular epoxy resins, with the aryl phosphate mixture and, where appropriate, with the appropriate parts by weight of other hardeners or hardener mixtures, and of other additives (see Table 1, for example), e.g. a solution of dicyandiamide at 10% strength by weight in DMF/methoxypropyl acetate (1:1) and a solution of methylimidazole at 20% strength by weight in methanol. For this, the resin preferably forms an initial charge, and suitable solvents are used, if required, to lower its viscosity and increase its ability to dissolve the additives. The method is generally to add all of the additives and homogenize the mixture with stirring and, if required, with warming to from about 20 to 70°. This mixture is then generally degassed and freed from excess solvent with stirring for from 5 to 10 minutes at from 20 to 100° C., preferably from 40 to 80° C. Curing then usually takes place for from about 1 to 4 hours at temperatures of from 60 to 160° C., preferably from 80 to 120° C., particularly preferably 100° C. and for from about 1 to 2 hours at temperatures of from 140 to 200° C., preferably from 160 to 190° C., particularly preferably at 180° C. All the operations may take place in small flat aluminium weighing dishes, for example.

The inventive aryl phosphate mixture may also be used to form a flame-retardant prepolymer. For this, the inventive aryl phosphate mixture is incorporated at a substoichiometric level into a polymer containing reactive groups, in particular epoxy and/or isocyanate groups. The term substoichiometric refers here to the aryl phosphate of type I of the mixture. The resultant prepolymer therefore has incomplete curing and is a flame-retardant prepolymer which can be used and cured. This prepolymer has the advantage of application-related properties which give it improved handling.

There is no need here for separate purchasing, storage and handling by the processor of a flame retardant which may require specific technical measures or measures related to workplace health and safety.

The inventive aryl phosphate mixture may moreover be incorporated into the polymers in such a way as to form what is known as a flame-retardant prepolymer. For this, the inventive aryl phosphate mixture is incorporated at a substoichiometric level into the polymer, with the result that the polymer bears reactive groups, such as epoxy groups or isocyanate groups, not all of which have reacted with the aryl phosphate type I, and which therefore remain available for complete curing.

The preparation of the aryl phosphate mixture and its incorporation into polymers, in particular epoxy resins, may take place continuously or batchwise.

The invention further relates to the use of the aryl phosphate mixtures as flame retardants for polymers. An epoxy resin may be used as polymer.

The epoxy resin compositions provided with the inventive aryl phosphate mixtures may in particular be used as casting and laminating resins for potting compositions and for printed circuit boards in the electronics sector.

The invention further provides a polymer compound obtainable by reacting polymers, in particular epoxy resins, with the inventive aryl phosphate mixture or separately with an aryl phosphate of the formula I and with an aryl phosphate of the formula II.

The invention further provides a polymer comprising the inventive aryl phosphate mixture.

The examples below provide further description of the invention:

EXAMPLES

Example 1

Preparation of an aminophenyl phosphate (an aryl phosphate type I) having about 8.6% by weight of base nitrogen (hereinafter termed "aminophenyl phosphate Example 1"; chemical name of principal component: bis(3-aminophenyl) phenyl phosphate).

1304 g (4.00 mol) of triphenyl phosphate and 872 g (8.00 mol) of 3-aminophenol form an initial charge under nitrogen in a dry 2l four-necked flask with stirrer, thermometer, 40-cm Vigreux column with distillation head, product condenser (temperature-controlled to 48° C.) and multiple vacuum receiver. The mixture is melted at 120° C. and treated with 2.8 g (0.07 mol) of sodium hydroxide and 7.1 g of Vulkanox® BHT from Bayer. A 2000 Pa vacuum is then applied and heating is slowly continued. Beginning at 155° C., phenol is distilled off with slight reflux. Once the temperature has reached 195° C., the vacuum is lowered to 300 Pa. 75 minutes after application of the vacuum, 756 g of phenol have been formed and phenol formation ceases. Stirring is continued for 20 minutes and the mixture is then cooled to about 120° C. and flushed with $N_2$. The crude product is poured onto a metal sheet, whereupon it crystallizes on cooling to give 1407 g of a pale brown solid. The crude product is recrystallized from 1000 ml of ethanol.

| Yield: | 953 g (68%) near-white powder |
| Melting point: | from 128–132° C. |
| $NH_2$ content: | 8.6% |

Examples 2 to 13

EP Resin Test Specimens and Test Results
Description of Production of EP Resin Test Specimens 100 parts by weight of an epoxy resin based on bisphenol A with an epoxy equivalent of 180 g are treated with the appropriate parts by weight of hardener or hardener mixture and other additives as in Table 2 and homogenized for 5 minutes with stirring and warming.

The solution used comprises dicyandiamide at 10% strength by weight in DMF/methoxypropyl acetate (1:1) and methylimidazole at 20% strength by weight in methanol.

The mixtures were degassed with stirring for 5 to 10 minutes at 100° C. and then cured for 1 hour at 140° C. and 1 hour at 160° C. All operations took place in flat aluminium weighing dishes.

Description of Tests:

The processability of the resin formulations was characterized by determining the B time (start of cobwebbing) on a temperature-controlled steel plate. For this, some drops of a resin formulation were placed in the depression of a steel plate temperature-controlled to 140° C., 160° C. or 180° C. At intervals of a few seconds, a small bar of a wood or metal which does not influence the reaction is dipped into the resin mixture and removed. If a string of resin adheres to the bar and does not then fall away, the crosslinking reaction has begun. The time to the start of curing is defined here as the B time.

The curing reactions of the resin formulations were followed using differential dynamic heat-flux calorimetry or DSC (from 20 to 300° C., heating rate: 10° C./min), and onset and peak temperature for curing have been listed in the table.

The glass transition temperature $T_G$ of the cured resin was determined. For this, specimens of the cured resins were studied by DSC, taking the value from the second pass. Each pass traversed from −100 to 200° C. The heating rate was 10° C./min.

To determine flame retardancy, LOI values were measured to ASTM D2863. The LOI values give the oxygen concentration of an oxygen/nitrogen mixture which only just supports the combustion of a material. Specimens of the cured resin formulations were used for this test.

Yellowness Index values were determined using a Minolta chroma meter. For this, the clear, fully reacted resin specimens having an identical thickness of about 1.2 mm were measured on the standard white colour area of the device.

Thermogravimetric analysis (TGA) was used to determine the weight loss of the cured resin. Thermogravimetric analysis is a thermoanalytical process in which the weight or change in weight of a specimen is measured as a function of temperature or of time, using a controlled temperature programme. This method utilizes what is known as a thermobalance, which allows the weight of a specimen to be followed continuously and recorded in a defined atmosphere during the heating procedure as a function of temperature or of time. Specimens of the cured resin formulations were used for the measurements. The heating range extended from 25 to 400° C. The heating rate was 10° C./min. The table gives the percentage weight loss measured at 300° C. and at 400° C.

The phosphorus and nitrogen contents of the resins were calculated using the idealized formulae for the starting materials.

values are also higher when the standard system comprises the same amounts of aryl phosphates type II (illustrated in Examples 3 to 5);

can achieve a lower level of discoloration after complete reaction than when using a standard system which comprises the same amounts of aryl phosphates type II;

can achieve higher glass transition temperatures than when using a standard system which comprises the same amounts of aryl phosphates type II; and when comparison is made with a standard system which comprises the same amounts of aryl phosphates type II, can achieve the higher phosphorus and nitrogen contents required for flame retardancy without impairment of glass transition temperatures.

TABLE 1

| Formulation constituents and test results | Curing with dicyandiamide | | | | Curing with aryl phosphate type I | | | | Curing with dicyandiamide and aryl-phosphate type II | | | |
|---|---|---|---|---|---|---|---|---|---|---|---|---|
| Examples | 2* | 3* | 4* | 5* | 6* | 7 | 8 | 9 | 10* | 11 | 12 | 13 |
| Epoxy novolac | 100.0 | 100.0 | 100.0 | 100.0 | 100.0 | 100.0 | 100.0 | 100.0 | 100.0 | 100.0 | 100.0 | 100.0 |
| Dicyandiamide (10% strength in DMF/methoxypropyl ac.) | 1.5 | 1.5 | 1.5 | 1.5 | | | | | 0.8 | 0.8 | 0.8 | 0.8 |
| Methylimidazole (20% strength in methanol) | 0.8 | 0.8 | 0.8 | 0.8 | 0.8 | 0.8 | 0.8 | 0.8 | 0.8 | 0.8 | 0.8 | 0.8 |
| Methyl ethyl ketone as diluent | 25.0 | 25.0 | 25.0 | 25.0 | 25.0 | 25.0 | 25.0 | 25.0 | 25.0 | 25.0 | 25.0 | 25.0 |
| Aminophenyl phosphate Example 1 = aryl phosphate type I | | | | | 50.0 | 50.0 | 50.0 | 50.0 | 25.0 | 25.0 | 25.0 | 25.0 |
| Bisphenol A bis(di-xylenyl phosphate) = aryl phosphate type II | | 10.0 | | | | 10.0 | | | | 10.0 | | |
| Fyrolflex BDP ® (bisphenol-A bis(diphenyl) phosphate) = aryl phosphate type II | | | 10.0 | | | | 10.0 | | | | 10.0 | |
| Disflamoll DPK ® (diphenyl cresyl phosphate) = aryl phosphate type II | | | | 10.0 | | | | 10.0 | | | | 10.0 |
| B time at 140° C. (min) | 3.5 | >35.0 | >35.0 | >35.0 | 15.5 | 17.0 | 19.5 | 20.0 | 24.0 | 27.0 | 30.0 | 29.0 |
| B time at 160° C. (min) | 1.8 | 35.0 | 38.0 | >38.0 | 6.0 | 6.5 | 8.0 | 9.8 | 9.0 | 10.0 | 11.0 | 11.5 |
| B time at 180° C. (min) | 1.0 | 14.0 | 19.0 | 21.0 | 2.3 | 2.5 | 2.8 | 3.5 | 4.0 | 4.5 | 5.5 | 6.0 |
| Start/onset of reaction from DSC (° C.) | 134.6 | 143.4 | 159.2 | 156.5 | 144.8 | 142.5 | 142.1 | 144.1 | 145.5 | 147.1 | 149.2 | 147.4 |
| Maximum/peak of reaction from DSC (° C.) | 146.7 | 190.6 | 193.9 | 190.1 | 183.1 | 183.9 | 185.1 | 184.5 | 187.7 | 190.0 | 190.7 | 190.1 |
| Weight loss at 300° C. from TGA (%) | 3.2 | 2.6 | 5.7 | 3.4 | 3.1 | 3.2 | 2.8 | 5.0 | 3.6 | 3.3 | 3.4 | 4.0 |
| Weight loss at 400° C. from TGA (%) | 12.6 | 24.3 | 28.1 | 25.9 | 32.6 | 34.2 | 33.9 | 35.2 | 33.1 | 35.7 | 33.6 | 34.3 |
| LOI values for EP formulations | 23.5 | 21.5 | 20.5 | 23.0 | 24.0 | 25.0 | 24.2 | 25.2 | 24.0 | 25.0 | 23.5 | 23.6 |
| Yellowness Index | 64.4 | 118.1 | 111.1 | 134.5 | 72.1 | 60.6 | 64.8 | 66.2 | 85.8 | 99.7 | 84.5 | 79.8 |
| Glass transition temp. DSC 2nd pass (° C.) | 145.5 | 63.5 | 76.2 | 71.1 | 154.5 | 140.3 | 140.8 | 132.6 | 156.9 | 138.4 | 144.5 | 132.2 |
| Phosphorus content, calculated (%) | 0.0 | 0.7 | 0.8 | 0.8 | 2.9 | 3.2 | 3.2 | 3.2 | 1.7 | 2.1 | 2.2 | 2.2 |
| Nitrogen content, calculated (%) | 1.2 | 1.1 | 1.1 | 1.1 | 2.8 | 2.6 | 2.6 | 2.6 | 2.2 | 2.0 | 2.0 | 2.0 |

Key:
Comparative examples have been indicated by "*".

These experiments confirm that the use of epoxy resins with a combination of aryl phosphate type I (aminophenyl phosphate Example 1, principal component bis(3-aminophenyl) phenyl phosphate) and aryl phosphate type II, as in Examples 7 to 9:

can achieve higher LOI values than use of dicyandiamide, which is often used in industry (hereinafter termed "standard system"), illustrated in Example 2; the LOI Examples 10 to 13 confirm that aryl phosphates type I (aminophenyl phosphate Example 1, principal component bis-(3-aminophenyl) phenyl phosphate) is also effective when used in combination with the standard hardener dicyandiamide. Together with aryl phosphates type II, the values obtained for LOI, glass transition temperatures, Yellowness Indices and phosphorus and nitrogen contents are superior to those for the standard system with the same amounts of aryl phosphates type II (in this connection compare Examples 3 to 5 with Examples 11 to 13).

Examples 14 to 16
Epoxy/Glass Fibre Laminate Test Specimens and Test Results
Description of Production of Laminate Test Specimens:

Besides the test specimens obtained from cured epoxy resin formulations using the formulations given in Table 1, glass fibre laminates based on epoxy resins were also produced and studied.

For this, the resin formulations listed in Table 2 were first prepared to give a processable impregnating resin. The resin forms an initial charge. Methyl ethyl ketone is added to lower the viscosity and facilitate the dissolution of flame retardant, hardener, activator and other additives. It is vital here that a completely clear, homogeneous impregnation resin mixture is obtained and is further processed without delay.

For the processing of the impregnating resins it has proven helpful to determine their reaction/curing curve by DSC and their B time in advance.

The impregnating resin forms an initial charge in a tank. Viscosity was adjusted with methyl ethyl ketone so that the proportion of resin in the prepreg is about 50% by weight after saturation and run-off or, if necessary, wipe-off of the solution from the glass fibre mats, removal of solvent and conversion to the B state.

CS Interglas US-style 7628 glass filament fabrics with silane mix finish have approximately DIN A4 format. They are impregnated in the tank, wiped, and dried in an Ex vacuum oven at 140° C., and converted to the B state (solvent-free, dry, no longer tacky). No formation of bubbles must occur here. Resin content is checked by weighing (weight of prepreg−weight of fabric=weight of resin).

To produce a laminate, each of 8 prepregs is pressed to give a composite of thickness about 1.6 mm (a prepreg being a term for fibre mats composed of glass fibres or glass filaments impregnated with hot-curing resins; these pre-impregnated mats may be hot- or cold-pressed in a further process with shaping, for example to give mouldings or a semifinished product). The pressing takes place in two or more stages. The material is first preheated without any substantial pressure (i.e. at from 0 to 500 000 Pa) for 5 minutes. The pressure is then increased to 3 MPa within from about 5 to 10 minutes, and complete curing finally takes place at 160° C. for 1 hour.

A hard-metallized high-speed saw blade is then used to saw test specimens of format about 125×12.5×1.6 mm from the laminates.
Description of Tests Processability was characterized by determining the B time (start of cobwebbing) on a temperature-controlled steel plate.

The curing reaction of the resin was followed by DSC (from 20 to 300° C., heating rate 10° C./min), and onset and peak temperature for the curing have been listed in the table.

The glass transition temperature $T_G$ of the cured resin or laminate was determined, the value utilized being that from the second pass from −100 to 200° C. at a heating rate of 10° C./min.

The moisture sensitivity and the heat resistance of the laminates were tested by storing test specimens in a water-vapour-saturated atmosphere for 20 minutes at about 116° C. (hereinafter "pressure cooker test") this being followed by immediate immersion for at least 6 seconds in a solder bath at about 260° C. (hereinafter "solder bath test").

The phosphorus and nitrogen contents of the resins were calculated using the idealized formulae for the starting materials.

The fire test utilized was the UL 94 Test of Underwriters Laboratories Inc. for Flammability of Plastic Materials for Parts in Devices and Appliances. The UL 94 test is very frequently utilized for assessing the suitability of the flame-retardant materials for the electrical and electronics sector. For each test, five test specimens of dimensions about 125×13×1.6 mm were sawn from the epoxy/glass fibre laminates. The test specimens were clamped vertically and subjected to two 10 s applications of a gas flame in accordance with the specifications.

The classification results from the following requirements:

TABLE 2

| Test criterion | V-0 | V-1 | V-2 |
|---|---|---|---|
| Afterflame time for each test specimen for both flame applications | ≦10 s | ≦10 s | ≦10 s |
| Total afterflame time of all of the 5 test specimens for both flame applications | ≦50 s | ≦250 s | ≦250 s |
| Afterflame time and afterglow time for each test specimen after the 2nd flame application | ≦30 s | ≦60 s | ≦60 s |
| Afterflame or afterglow of any test specimen up to the holding clamp | no | no | no |
| Cotton pad ignited by drips or drops | no | no | yes |

TABLE 3

| | Examples | | |
|---|---|---|---|
| Constituents with amounts given in parts by weight | 14* | 15 | 16 |
| Epoxy novolac, semisolid | 100.0 | 100.0 | 100.0 |
| Methyl ethyl ketone | 25.0 | 25.0 | 25.0 |
| Aminophenyl phosphate Example 1 (principal component bis(3-aminophenyl) phenyl phosphate) = aryl phosphates type I | 50.0 | 50.0 | 50.0 |
| Methylimidazole (20% strength in methanol) | 0.8 | 0.8 | 0.8 |
| Bisphenol A bis(dixylenyl phosphate) = aryl phosphates type II | | 10.0 | 10.0 |
| Alumina trihydrate | | | 10.0 |
| B time at 160° C. (min) | 7.5 | 8.0 | 7.0 |
| B time at 180° C. (min) | 3.0 | 3.7 | 3.5 |
| Start/onset of reaction from DSC (° C.) | 139.9 | 137.8 | 141.5 |
| Maximum/peak of reaction from DSC (° C.) | 184.5 | 185.4 | 186.3 |
| Glass transition temperature from DSC (° C.) | 146.7 | 129.9 | 137.5 |
| Pressure cooker test, 20 min at about 116° C. | OK | OK | OK |
| Solder bath test, 6 s at about 260° C. | OK | OK | OK |
| Phosphorus content, calculated (%) | 2.4 | 2.7 | 2.6 |
| Nitrogen content, calculated (%) | 2.6 | 2.5 | 2.3 |
| UL 94 fire test | n.p. | n.p. | V-1 |

Key:
Comparative examples have been indicated by "*".
OK = acceptable, i.e. no visible damage to test specimen, e.g. bubble formation, delamination, discoloration, etc.
n.p. = not passed, i.e. the afterflame times exceeded the limits of the standard.

The experiments confirm that use of epoxy resin/glass fibre laminates with a combination of aryl phosphates type I (aminophenyl phosphate Example 1, principal component bis(3-aminophenyl) phenyl phosphate), arylphosphates type II and alumina trihydrate can achieve V-1 flame retardancy to UL 94. Classification V-1 is narrowly missed without alumina trihydrate.

Example 17

Preparation of an aminophenyl phosphate (aryl phosphates type 1) having about 11.5% of basic nitrogen (hereinafter termed "aminophenyl phosphate Example 17"; principal component tris(3-aminophenyl) phosphate):

489 g (1.50 mol) of triphenyl phosphate and 490 g (4.5 mol) of 3-aminophenol form an initial charge under nitrogen in a dry 1l four-necked flask with stirrer, thermometer, 40-cm Vigreux column with distillation head, product condenser (temperature-controlled to 48° C.) and multiple vacuum receiver. The mixture is melted at 120° C. and treated with 1.5 g (0.04 mol) of sodium hydroxide and 2.8 g of Vulkanox® BHT from Bayer. A 2000 Pa vacuum is then applied and heating is slowly continued. Beginning at 155° C., phenol is distilled off with slight reflux. Once the temperature has reached 195° C., the vacuum is lowered to 300 Pa. 75 minutes after application of the vacuum, 402 g of phenol have been formed and phenol formation ceases. Stirring is continued for 20 minutes and the mixture is then cooled to about 120° C. and flushed with $N_2$. The crude product is poured onto a metal sheet, whereupon it crystallizes on cooling to give 595 g of a pale brown solid. The crude product is recrystallized from 1000 ml of ethanol.

| Yield: | 357 g (60%) beige powder |
|---|---|
| Melting point: | from 145–148° C. |
| $NH_2$ content: | 11.5% |

Examples 18 to 20

Epoxy/Glass Fibre Laminate Test Specimens and Test Results

The laminate test specimens were produced and tested as described above under Examples 14 to 16.

TABLE 4

| Constituents with amounts given in parts by weight | Examples | | |
|---|---|---|---|
|  | 18* | 19 | 20 |
| Epoxy novolac, semisolid | 100.0 | 100.0 | 100.0 |
| Methyl ethyl ketone | 25.0 | 25.0 | 25.0 |
| Aminophenyl phosphate Example 17 (principal component tris(3-aminophenyl) phosphate) = aryl phosphates type I | 35.0 | 35.0 | 35.0 |
| Methylimidazole (20% strength in methanol) | 0.8 | 0.8 | 0.8 |
| Bisphenol A bis(dixylenyl phosphate) = aryl phosphates type II |  | 10.0 | 10.0 |
| Alumina trihydrate |  |  | 10.0 |
| B time at 160° C. (min) | 360 | 480 | 330 |
| B time at 180° C. (min) | 105 | 150 | 135 |
| Start/onset of reaction from DSC (° C.) | 135.9 | 143.3 | 142.2 |
| Maximum/peak of reaction from DSC (° C.) | 186.5 | 189.3 | 188.6 |
| Glass transition temperature from DSC (° C.) | 176.3 | 159.6 | 159.2 |
| Pressure cooker test, 20 min at about 116° C. | OK | OK | OK |
| Solder bath test, 6 s at about 260° C. | OK | OK | OK |
| Phosphorus content, calculated (%) | 2.1 | 2.5 | 2.4 |
| Nitrogen content, calculated (%) | 3.1 | 2.9 | 2.7 |
| UL 94 fire test | n.p. | V-1 | V-1 |

Key:
Comparative examples have been indicated by "*".
OK = acceptable, i.e. no visible damage to test specimen, e.g. bubble formation, delamination, discoloration, etc.
n.p. = not passed, i.e. the afterflame times exceeded the limits of the standard.

The experiments confirm that the use of epoxy resin/glass fibre laminates with a combination of aryl phosphates type I (aminophenyl phosphate-Example 17, principal component tris(3-aminophenyl) phosphate) and aryl phosphates type II can achieve V-1 flame retardancy to UL 94.

When aminophenyl phosphate Example 1 (principal component bis(3-aminophenyl) phenyl phosphate) is used, concomitant use of alumina trihydrate is also needed for classification V-1, as shown by Examples 15 and 16. When use is made of aminophenyl phosphate Example 17 (principal component tris(3-aminophenyl) phosphate), the classification V-1 is achieved solely via combination with an aryl phosphate type II.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Aryl phosphate mixture comprising aryl phosphates type I of the general formula (I)

$$\left[ \begin{array}{c} R^1 \\ \phantom{x} \\ R^2 \end{array} \!\!\!\!\!\bigcirc\!\!\!\!\!-O \right]_n \!\!\! \begin{array}{c} Y \\ \| \\ P \\ \end{array} \!\!\! \left[ O-\!\!\!\!\!\bigcirc\!\!\!\!\! \begin{array}{c} R^3 \\ \phantom{x} \\ R^4 \end{array} \right]_{3-n} \quad (I)$$

where
R¹ to R⁴, independently of one another, are hydrogen, alkyl, cycloalkyl, alkenyl, aralkyl or aryl, where the aryl moiety is optionally unsubstituted or have alkyl substitution,
Y is oxygen or sulphur,
X is OH, SH, COOH, COOR⁵, $NH_2$, NHR⁶, NR⁶R⁷ or CN,
where R⁵ to R⁷, independently of one another, are as defined for R¹ to R⁴, and
n is 0, 1 or 2, and
aryl phosphates type II of the general formula (II)

$$(II)$$

where
R⁸ to R¹⁵, independently of one another, are hydrogen, alkyl, cycloalkyl, alkenyl, aralkyl or aryl, where the aryl moiety is optionally unsubstituted or have alkyl substitution,
m is 0, 1, 2 or 3 and
A is aromatics which contain at least two functional groups.

2. Aryl phosphate mixture according to claim 1, where for the aryl phosphates type I, R¹ to R⁴, independently of one another, are a $C_1$–$C_{20}$-alkyl radical, a $C_5$–$C_8$-cycloalkyl radical, a linear or branched $C_2$–$C_{12}$-alkenyl radical, a $C_7$–$C_{12}$-aralkyl group, or $C_6$–$C_{14}$-aryl radicals, where the aryl radicals is optionally unsubstituted or have substitution by $C_1$–$C_4$-alkyl radicals.

3. Aryl phosphate mixture according to claim 1, where for the aryl phosphates type I, R¹ to R⁴, independently of one another, are a $C_1$–$C_4$-alkyl radical, a $C_5$–$C_6$-cycloalkyl radical, a linear or branched $C_2$–$C_6$-alkenyl radical, a $C_7$–$C_{12}$-aralkyl group, or $C_6$–$C_{14}$-aryl radicals, where the aryl radicals is optionally unsubstituted or have substitution by $C_1$–$C_4$-alkyl radicals.

4. Aryl phosphate mixture according to claim 1, where for the aryl phosphates type I, $R^1$ to $R^4$, independently of one another, are methyl, ethyl, propyl, isopropyl, n-butyl, isobutyl, tert-butyl, pentyl, hexyl, octyl, dodecyl, tetradecyl, eicosyl, cyclopentyl, cyclohexyl, methylcyclohexyl, vinyl, prop-1-enyl, prop-2-enyl, n-but-3-enyl, n-pent-4-enyl, n-hex-5-enyl, phenyl, naphthyl, biphenyl, benzyl, methylbenzyl, or phenylethyl.

5. Aryl phosphate mixture according to claim 1, where for the aryl phosphates type I, X is $NH_2$, the radicals $R^1$ to $R^4$ are hydrogen and n is 0, 1 or 2.

6. Aryl phosphate mixture according to claim 1, where for the aryl phosphates type II, $R^5$ to $R^{12}$, independently of one another, are a $C_1$–$C_{20}$-alkyl radical, a $C_5$–$C_8$-cycloalkyl radical, a linear or branched $C_2$–$C_{12}$-alkenyl radical, a $C_7$–$C_{12}$-aralkyl group, or a $C_6$–$C_{14}$-aryl radical, where the aryl radical is optionally unsubstituted or have substitution by $C_1$–$C_4$-alkyl radicals.

7. Aryl phosphate mixture according to claim 1, where for the aryl phosphates type II, $R^5$ to $R^{12}$, independently of one another, are methyl, ethyl, propyl, isopropyl, n-butyl, isobutyl, tert-butyl, pentyl, hexyl, octyl, dodecyl, tetradecyl, eicosyl, cyclopentyl, cyclohexyl, methylcyclohexyl, vinyl, prop-1-enyl, prop-2-enyl, n-but-3-enyl, n-pent-4-enyl, n-hex-5-enyl, phenyl, naphthyl, biphenyl, benzyl, methylbenzyl, or phenylethyl.

8. Aryl phosphate mixture according to claim 1, where for the aryl phosphates type II, the phosphates are unbridged or bridged.

9. Aryl phosphate mixture according to claim 1, where use is made of triphenyl phosphate or alkylphenyl phosphates as aryl phosphates type II.

10. Aryl phosphate mixture according to claim 1, where a radical which in the form of $A(OH)_2$ is the compound bisphenol A or resorcinol is used as A for the aryl phosphates type II.

11. Aryl phosphate mixture according to claim 1, where the amounts mixed of the aryl phosphates type I are from 3 to 98% by weight, and the amounts mixed of the aryl phosphates type II are from 2 to 97% by weight, based in each case on the entirety of aryl phosphates type I and aryl phosphates type II.

12. Aryl phosphate mixture according to claim 1, where the mixture comprises from 70 to 100% by weight of aryl phosphates type I and aryl phosphates type II, based on the mixture.

13. Process for preparing mixtures according to claim 1, comprising mixing aryl phosphates type I of the general formula (I)

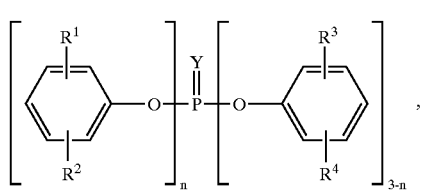

(I)

where $R^1$ to $R^4$, Y, X and n are as defined in claim 1, and aryl phosphates type II of the general formula (II)

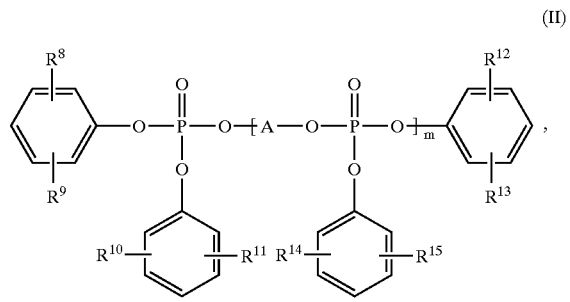

(II)

where $R^8$ to $R^{15}$, A and m are as defined in claim 1.

14. Process for preparing polymers provided with flame retardant, comprising incorporating the aryl phosphate mixture according to claim 1 or the aryl phosphates type I and II separately into the polymer.

15. Process for preparing polymers provided with flame retardant according to claim 14, wherein the amounts of the aryl phosphate mixture incorporated into the polymer are from 2 to 80% by weight, based on the polymer.

16. Process for preparing polymers provided with flame retardant according to claim 14, comprising incorporating amounts of from 1 to 50% by weight, of the aryl phosphates type II and amounts of from 1 to 30% by weight, of the aryl phosphates type II, based on the polymers, separately into the polymer.

17. Process for preparing polymers provided with flame retardant according to claim 14, comprising incorporating the aryl phosphate mixture or aryl phosphates type I and II separately into the polymers at a temperature of from 20 to 200° C.

18. Process for preparing polymers provided with flame retardant according to claim 17, wherein the polymer is an epoxy resin.

19. Process for preparing hardener mixtures provided with flame retardant for epoxy resins, comprising reacting amounts of from 10 to 100% by weight, of aryl phosphate mixture according to claim 1 and amounts of from 0 to 90% by weight, of anhydride hardener or of amine hardener, where the total of the % by weight of the aryl phosphate mixture and of the anhydride hardener or amine hardener is 100% by weight, based on the hardener mixtures.

20. A process of retarding flames comprising providing the aryl phosphate mixtures according to claim 1 as flame retardants for polymers.

21. The process according to claim 20, wherein epoxy resins are used as polymers.

22. Polymer compound obtainable by reacting-epoxy resins with the aryl phosphate mixture of claim 1 or separately with the aryl phosphates of the formulae I and II.

23. Polymers comprising an aryl phosphate mixture of claim 1.

* * * * *